US008641415B2

(12) United States Patent  (10) Patent No.: US 8,641,415 B2
Kallis  (45) Date of Patent: Feb. 4, 2014

(54) METHOD AND APPARATUS FOR TOOTH CRACK DETECTION BY MEANS OF ACOUSTIC EMISSION

(75) Inventor: James M. Kallis, Los Angeles, CA (US)

(73) Assignee: Kallis Technical Services, Los Angeles, CA (US)

( * ) Notice: Subject to any disclaimer, the term of this patent is extended or adjusted under 35 U.S.C. 154(b) by 331 days.

(21) Appl. No.: 12/983,779

(22) Filed: Jan. 3, 2011

(65) Prior Publication Data

US 2011/0177471 A1   Jul. 21, 2011

Related U.S. Application Data

(60) Provisional application No. 61/336,054, filed on Jan. 17, 2010.

(51) Int. Cl.
 *A61C 17/00* (2006.01)
(52) U.S. Cl.
 USPC .............................. 433/80; 433/215; 600/587
(58) Field of Classification Search
 USPC .................................................. 433/80, 215
 See application file for complete search history.

(56) References Cited

U.S. PATENT DOCUMENTS

| | | | |
|---|---|---|---|
| 3,393,676 A | 7/1968 | Kummer et al. | |
| 3,713,127 A | 1/1973 | Keledy et al. | |
| 3,874,083 A | 4/1975 | Buckley | |
| 4,014,100 A | 3/1977 | Spotteck | |
| 4,176,454 A * | 12/1979 | Hatter et al. | 433/119 |
| 4,204,978 A | 5/1980 | Ibsen et al. | |
| 4,500,294 A | 2/1985 | Lewis | |
| 4,828,494 A | 5/1989 | Angus et al. | |
| 5,742,700 A | 4/1998 | Yoon et al. | |
| 5,874,677 A | 2/1999 | Bab et al. | |
| 6,062,083 A | 5/2000 | Dunegan | |
| 6,102,704 A | 8/2000 | Eibofner et al. | |
| 6,213,958 B1 | 4/2001 | Winder | |
| 6,231,338 B1 | 5/2001 | de Josselin de Jong et al. | |
| 6,437,334 B1 | 8/2002 | Thomas et al. | |
| 6,491,522 B1 | 12/2002 | Jensen | |
| 7,270,543 B2 | 9/2007 | Stookey et al. | |
| 7,285,091 B2 | 10/2007 | Blodgett et al. | |

(Continued)

OTHER PUBLICATIONS

Dunegan Engineering Company "AE Waveguides" DECI Report Mar. 2006.*

(Continued)

*Primary Examiner* — Max Hindenburg
*Assistant Examiner* — Renee Danega
(74) *Attorney, Agent, or Firm* — Lewis B. Sternfels

(57) ABSTRACT

In a method and apparatus for detecting a crack in a human tooth, especially one covered by a restoration, such as a crown, the approach is to stress the suspect tooth and, by means of acoustic emission techniques, analyze the characteristics of the resultant acoustic emission from the tooth. To aid the identification of a crack from the acoustic emission signal, a baseline may be obtained by performing this procedure at a time when the tooth is known not be cracked, e.g., when a restoration is placed on it. This baseline acoustic emission signature is recorded. This procedure is repeated at intervals. The subsequent measurements are compared with the baseline to identify changes that indicate the initiation and growth of a crack. The invention includes apparatus for implementing the method. The approach is to integrate the acoustic emission pulser and sensor into commercially available dental instruments, e.g., a tooth polisher and a water syringe.

18 Claims, 4 Drawing Sheets

(56) References Cited

U.S. PATENT DOCUMENTS

| | | | |
|---|---|---|---|
| 7,303,397 | B2 | 12/2007 | Boutoussov |
| 7,311,521 | B2 | 12/2007 | Boston |
| 7,577,284 | B2 | 8/2009 | Wong et al. |
| 2011/0159460 | A1* | 6/2011 | Miller ............... 433/118 |

OTHER PUBLICATIONS

Mutlu et al. "The effect of box preparation on the strength of glass-fiber reinforced composite inlay-retained fixed partial dentures" Apr. 2005, The Journal of Prosthetic Dentistry, pp. 227-343.*

Culjat et al., "Ultrasound crack detection in a simulated human tooth", Dentomaxillofacial Radiology, 34, 80-85, 2005.

Singh et al., "Penetration of radiopaque dental restorative materials using a novel ultrasound imaging system", American Journal of Dentistry, 20(4):221-6, Aug. 2007.

Culjat et al., "Ultrasound detection of submerged dental implants through soft tissue in a porcine model", Journal of Prosthetic Dentistry, 99, 218-224, Mar. 2008.

Franke et al., "Acoustic Emission Measurement System for the Orthopedical Diagnostics of the Human Femur and Knee Joint", www.bonedias.de/downloads/ewgae_2004_franke.pdf.

Physical Acoustics Corp., "Acoustic Emission Sensors", http://www.pacndt.com/index.aspx?go=products&focus=Sensors.htm.

Physical Acoustics Corp., "Miniature Sensors", http://www.pacndt.com/index.aspx?go=products&focus=/sensors/miniature.htm.

Dunegan Engineering Company Inc., "AE Waveguides", DECI Report, Mar. 2006.

Dunegan Engineering Company Inc., "AE SMART 2000", 2000.

Physical Acoustics Corp., "Complete Acoustic Emission Product Line", http://www.pacndt.com/index.aspx?go=products.

Physical Acoustics Corp., "Acoustic Emission Testing and Analysis Software", http://wvvw.pacndt.com/index.aspx?go=products&focus=Software.htm.

* cited by examiner

METHOD AND APPARATUS FOR TOOTH CRACK DETECTION BY MEANS OF ACOUSTIC EMISSION

CROSS-REFERENCE TO RELATED APPLICATION

This application claims the benefit of U.S. Provisional Application No. 61/336,054, filed 17 Jan. 2010.

REFERENCE REGARDING FEDERAL SPONSORSHIP

Not Applicable

REFERENCE TO MICROFICHE APPENDIX

Not Applicable

BACKGROUND OF THE INVENTION

1. Field of the Invention

The present invention relates to a method and apparatus for tooth crack detection and, more particularly, to such detection by means of acoustic emission and further to detection of a crack in a tooth covered by a restoration.

2. Description of Related Art and Other Considerations
References Cited

U.S. PATENT DOCUMENTS

| | | | |
|---|---|---|---|
| 3,713,127 | Jan. 1973 | Keledy et al. | 340/261 |
| 4,204,978 | May 1980 | Ibsen et al. | 252/408 |
| 4,500,294 | Feb. 1985 | Lewis | 433/215 |
| 4,828,494 | May 1989 | Angus et al. | 433/215 |
| 5,742,700 | Apr. 1998 | Yoon et al. | 382/128 |
| 5,874,677 | Feb. 1999 | Bab et al. | 73/629 |
| 6,062,083 | May 2000 | Dunegan | 73/587 |
| 6,102,704 | Aug. 2000 | Eibofner et al. | 433/215 |
| 6,213,958 B1 | Apr. 2001 | Winder | 600/586 |
| 6,231,338 B1 | May 2001 | de Josselin de Jong et al | 433/29 |
| 6,437,334 B1 | Aug. 2002 | Thomas et al. | 250/341.6 |
| 6,491,522 B1 | Dec. 2002 | Jensen | 433/215 |
| 7,270,543 B2 | Sep. 2007 | Stookey et al. | 433/215 |
| 7,285,091 B2 | Oct. 2007 | Blodgett et al. | 600/437 |
| 7,303,397 B2 | Dec. 2007 | Boutoussov | 433/215 |
| 7,311,521 B2 | Dec. 2007 | Boston | 433/37 |
| 7,577,284 B2 | Aug. 2009 | Wong et al. | 382/128 |

Other Publications

Culjat et al., "Ultrasound crack detection in a simulated human tooth", Dentomaxillofacial Radiology, 34, 80-85, 2005.

Singh et al., "Penetration of radiopaque dental restorative materials using a novel ultrasound imaging system", American Journal of Dentistry, 20(4):221-6, August 2007.

Culjat et al., "Ultrasound detection of submerged dental implants through soft tissue in a porcine model", Journal of Prosthetic Dentistry, 99, 218-224, March 2008.

Franke et al., "Acoustic Emission Measurement System for the Orthopedical Diagnostics of the Human Femur and Knee Joint", www.bonedias.de/downloads/ewgae_2004_franke.pdf.

Physical Acoustics Corp., "Acoustic Emission Sensors", http://www.pacndt.com/index.aspx?go=products&focus=Sensors.htm.

Physical Acoustics Corp., "Miniature Sensors", http://www.pacndt.com/index.aspx?go=products&focus=/sensors/miniature.htm.

Dunegan Engineering Company Inc., "AE Waveguides", DECI Report, March 2006.

Dunegan Engineering Company Inc., "AE SMART 2000", 2000.

Physical Acoustics Corp., "Complete Acoustic Emission Product Line", http://www.pacndt.com/index.aspx?go=products.

Physical Acoustics Corp., "Acoustic Emission Testing and Analysis Software", http://www.pacndt.com/index.aspx?go=products&focus=Software.htm.

DISCUSSION

An initial crack in a tooth could grow sufficiently to fracture the tooth. Aside from producing great pain to the person, the consequence for the patient would be extensive and expensive dental work, which could include endodontic, periodontic, and restorative work. Accordingly, it is advantageous and necessary to detect a crack in a tooth as soon as possible after the initiation of a crack.

The state of the art of tooth crack detection in 2005 was described by the Dental Ultrasound Imaging Group of UCLA (University of California, Los Angeles) (see above-referenced Culjat et al., "Ultrasound crack detection in a simulated human tooth"), as follows:

"The detection and diagnosis of fractures in teeth are vexing and difficult clinical problems. Currently, dentists use patient history, visual examination, and a comprehensive endodontic examination to diagnose cracked teeth. However, clinical signs and symptoms are highly variable and are often insufficient to reach an unequivocal diagnosis. Cracks often cannot be visualized from the external surface of a tooth. Furthermore, cracks that are visible on the surface enamel often stop at the dentino-enamel junction (DEJ) and are of no clinical consequence. Sometimes invasive procedures such as raising a mucoperiosteal flap or creating an endodontic access cavity, in combination with transillumination, staining, or microscopy, are used to visualize cracks, but some cracks still may not be identified. Differentiating between a shallow inconsequential crack and a 'through and through fracture' is often extremely problematic. Although presence of a visible fracture line in enamel and a high ratio of restoration to total natural crown volume are associated with increased incidence of tooth fracture, this finding applies to a patient population, not to the diagnosis of cracks in each individual patient. Dental radiographs or microtomographs do not usually show cracks themselves, only their subsequent bony damage after a crack has eventually been colonized by bacteria and become a source of inflammation or infection. Optical coherence tomography and electric conductance methods are poorly suited to deep crack detection. The development of methods for the assessment of cracked teeth and root fractures has been specifically identified as a top research priority by the American Association of Endodontists Foundation."

Therefore, the early detection of a crack is more difficult with regards to a tooth covered by a restoration and, accordingly, the early detection of a crack in a tooth covered by a restoration is not only desirous, but essential.

Prior art tooth crack detectors are disclosed in the following U.S. Patents (all of which are incorporated by reference):

| 4,204,978 | May 1980 | Ibsen et al. | 252/408 |
| 4,828,494 | May 1989 | Angus et al. | 433/215 |
| 6,437,334 B1 | Aug. 2002 | Thomas et al. | 250/341.6 |
| 6,491,522 B1 | Dec. 2002 | Jensen | 433/215 |

Each uses a distinct method:
Dye stain (Ibsen)
Biting on a ball (Angus)
Thermal imaging of ultrasonically heated tooth (Thomas)
Electrical conductance measurement (Jensen).

None of these patented methods can, in the early stage of crack growth, detect and locate a crack in a tooth covered by a restoration for the following reasons.

The Ibsen and Thomas methods require that the crack be seen. This requirement rules out such methods for a subsurface crack or a crack covered by a restoration.

The Angus method does not provide for early detection, because the crack causes pain only when the tooth is on the verge of fracturing, as based upon the inventor's personal experience with several of his teeth, and corroborated by Lisa Chan Flagg, DDS, who states [personal communication (E-mail message), Jan. 31, 2009]: "By the time a patient experiences pain, the tooth is already fractured." Furthermore, the Angus method is not capable of locating the crack.

The Jensen method involves the application of a direct current voltage to a tooth by means of a dental tool and the completion of an electrical circuit by means of a return connector, which " . . . can take the form of a lip clip, a shoulder plate, or a hand-held connector". This method would not work for a tooth covered by a metallic crown because, if the dental tool were placed on the metal, the low resistance of the crown would divert the electrical current flow along the metal, thus preventing a significant fraction of the current from flowing through the high-resistance tooth itself. This phenomenon occurs because the metal and the tooth are electrical resistors in parallel. The over-all electrical resistance of this portion of the circuit is given by $R=R_{metal}/[(R_{metal}/R_{tooth})+1]$. If $[(R_{metal}/R_{tooth})<<1$, then $R \approx R_{metal}/(0+1)=R_{metal}$. Therefore, the over-all electrical resistance R is nearly equal to that of the metal restoration and, as a result of this fact, R is insensitive to changes in the high resistance $R_{tooth}$ as produced by a crack.

In addition to the tooth crack detectors disclosed in the patent literature, an ultrasound imaging tooth crack detector is disclosed in papers by the UCLA Dental Ultrasound Imaging Group, e.g.:
1. Culjat et al., "Ultrasound crack detection in a simulated human tooth", Dentomaxillofacial Radiology, 34, 80-85, 2005;
2. Singh et al., "Penetration of radiopaque dental restorative materials using a novel ultrasound imaging system", American Journal of Dentistry, 20(4):221-6, August 2007; and
3. Culjat et al., "Ultrasound detection of submerged dental implants through soft tissue in a porcine model", Journal of Prosthetic Dentistry, 99, 218-224, March 2008.

The ultrasound imaging technique consists of transmitting acoustic waves through a coupling agent, whose acoustic impedance matches that of the tooth, into the tooth and detecting the reflected waves. These reflections (acoustic echo returns) result from discontinuities. A normal tooth produces a reflection at the couplant-enamel interface, followed by one at the dentino-enamel junction (DEJ). A tooth having a crack below the DEJ produces an additional reflection following that from the DEJ; the depth of the crack can be calculated as a function of the time interval between the DEJ echo and the crack echo. The UCLA ultrasound technique documented in the three above-mentioned papers can find cement defects beneath crowns, but not deep cracks beneath such crowns referenced therein.

Prior art tooth caries detectors are disclosed in the following U.S. Patents (all of which are incorporated by reference):

| 4,500,294 | Feb. 1985 | Lewis | 433/215 |
| 5,874,677 | Feb. 1999 | Bab et al. | 73/629 |
| 6,102,704 | Aug. 2000 | Eibofner et al. | 433/215 |
| 6,231,338 B1 | May 2001 | de Josselin de Jong et al. | 433/29 |
| 7,270,543 B2 | Sep. 2007 | Stookey et al. | 433/215 |
| 7,285,091 B2 | Oct. 2007 | Blodgett et al. | 600/437 |
| 7,303,397 B2 | Dec. 2007 | Boutoussov | 433/215 |
| 7,311,521 B2 | Dec. 2007 | Boston | 433/37 |
| 7,577,284 B2 | Aug. 2009 | Wong et al. | 382/128 |

None of these patented methods can detect and locate caries underneath a restoration for the following reasons.
1. Lewis' method is to bring a temperature sensitive material into contact with the patient's teeth to " . . . visibly indicate a temperature differential between teeth in close proximity to each other". A restoration would mask this temperature differential.
2. The methods of Bab et al. and Boston have limitations. The method disclosed by Bab et al. is limited to " . . . the detection of smooth surface lesions of dental caries on a tooth crown surface". Boston's method is limited to the " . . . diagnosis of enamel cavitation of an interproximal dental surface." Therefore, neither is applicable to the detection of subsurface cracks.
3. The methods of Eibofner et al., de Josselin de Jong et al., Stookey et al., Blodgett et al., Boutoussov, and Wong et al. involve illuminating the tooth. A restoration would block the light.

Therefore, a novel approach to early detection of a crack in a tooth covered by a restoration is needed.

SUMMARY OF THE INVENTION

This invention comprises a method and apparatus for detecting a crack in a human tooth and, also, a tooth covered by a restoration (e.g., a crown). The approach is to stress the suspect tooth, causing the crack to grow and, thereby, to emit acoustic waves, and to analyze the characteristics of the resultant acoustic emission from the tooth. To detect the crack by means of acoustic emission (AE), stress waves are emitted by rapid structural changes in material or a solid body. Stress on a crack causes the crack to grow and "talk", i.e., to emit acoustic waves, which can be detected by a sensor. The characteristic acoustic emission signal produced by crack initiation or growth is a very short rise time and an exponential decrease of the amplitude (see, for example, the above-cited Franke et al. "Acoustic Emission Measurement System for the Orthopedical Diagnostics of the Human Femur and Knee Joint.") Analysis of the AE signal can be employed to detect the presence of a crack in the body.

To aid the identification of a crack from the acoustic emission signal, a baseline acoustic emission may be obtained by performing this procedure at a time when the tooth is known not be cracked, e.g., when a restoration is placed on it. This baseline acoustic emission forms a signature which is recorded. This stressing and analyzing procedure is repeated at timed or periodic intervals. The subsequent measurements are compared with the baseline signature to identify any changes that might indicate the initiation and growth of a crack.

The present invention further includes apparatus for implementing this method, by integrating the stressor and acoustic emission sensor into commercially available dental instruments, e.g., a tooth polisher and a water syringe.

Several advantages, including those over the prior art, are obtained and derived from these arrangements. A crack is detected before it grows large enough to cause pain, and as soon as possible after the initiation of the crack. Such detection is feasible even when the tooth is covered by a restoration.

Although AE has been used extensively since at least the 1970s as a nondestructive testing technique to detect cracks in large structures, such as bridges and pressure vessels (e.g., see Keledy et al. U.S. Pat. No. 3,713,127) and also, since at least the early 1970s, to bones (e.g., see Winder U.S. Pat. No. 6,213,958), there appears to be no prior art on applying AE to human teeth. Further, as relating to the application of AE to bones (e.g., as discussed in Winder patent U.S. Pat. No. 6,213,958 and other relevant publications, there is no known design that can reasonably be applied to teeth, as presenting such difficulties as (1) placing the AE sensor in intimate contact with the tooth, which problem has yet to be solved or even addressed in the prior art, and (2) obtaining information regarding the growth of the crack in the form of an acoustic signal. As also distinguished from the Winder patent disclosure, the present invention includes a method for overcoming these such difficulties.

The method of AE crack detection, as presented herein, differs from prior art ultrasound imaging. With ultrasound imaging, the acoustic waves are transmitted into the body of the tooth. The outgoing signal consists of the echo, i.e., the reflection from the crack. The present inventive method is distinguishable from the above-referenced Singh et al. publication, "Penetration of radiopaque dental restorative materials using a novel ultrasound imaging system", as evidenced by the following description taken therefrom:

"Dental ultrasound faces the unique challenges of: large acoustic losses and reverberations due to considerable impedance mismatches within teeth, including those among dentin, enamel, water-filled cracks, restorative materials, pulp, and periodontal ligament; acoustic clutter resulting from the complex microstructure and irregular macrostructure of teeth; a small unambiguous range due to high compressional sound velocities in hard tissues; lack of a suitable high impedance acoustic couplant; varied and complex surface conformations; and the relatively small dimensions of teeth and dental pathologies."

With AE, as employed in the present invention, the acoustic waves are emitted from the body of the tooth. The signal comprises the acoustic emission from the crack, as applied stresses on the tooth cause growth in the crack. Consequently, AE can detect a subsurface crack, and a large AE signal can be transmitted even through a restoration covering the tooth.

Other aims and advantages, as well as a more complete understanding of the present invention, will appear from the following explanation of exemplary embodiments and the accompanying drawings thereof.

DETAILED DESCRIPTION OF THE INVENTION

Figure 1:
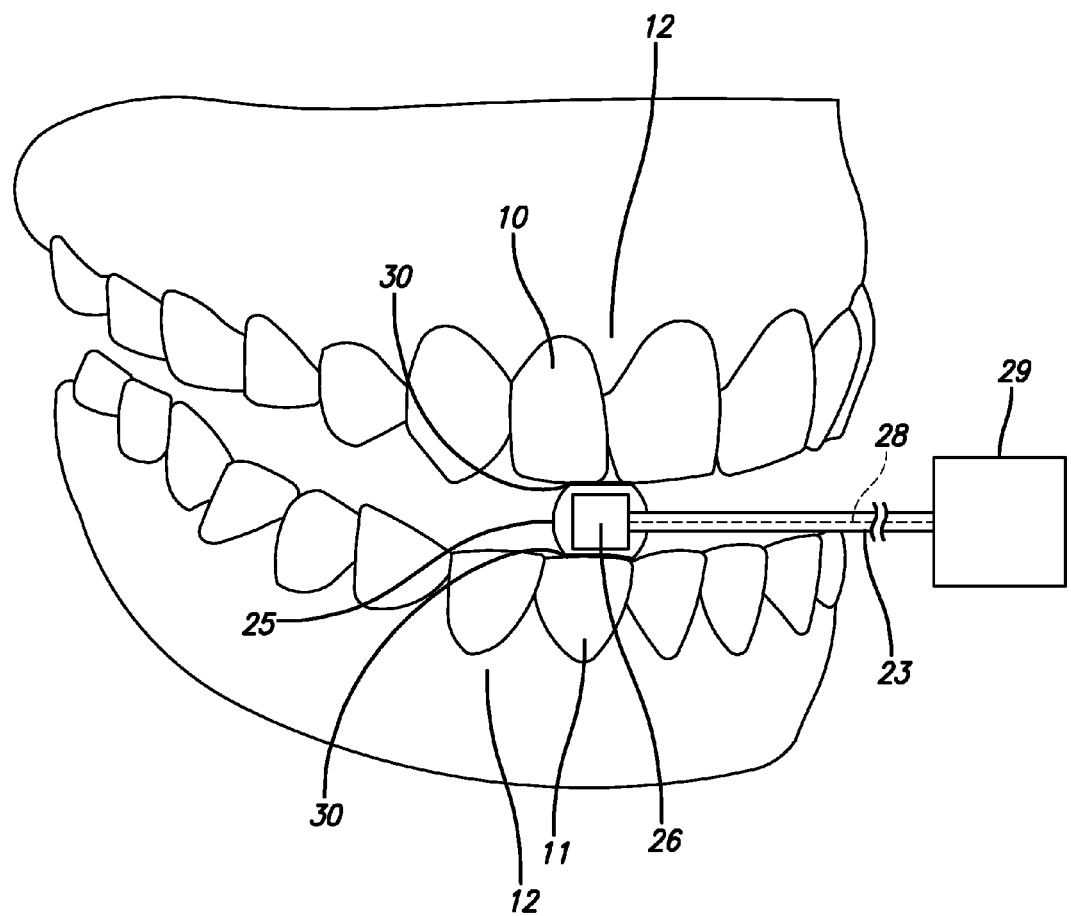
FIG. 1 shows a first embodiment of the apparatus of the invention in use, in which the acoustic emission signal is produced by the patient biting on an acoustic emission sensor. The illustrated device is symmetrical about an axis passing along the cable attached thereto.

The apparatus to implement AE crack detection comprises:
1. Tooth stressing: This is accomplished in a different way in each embodiment, namely, in the first embodiment, by biting by the patient on an object, in the second embodiment, by pressing on the tooth, and in the third embodiment, by emitting a pulse from the sensor, i.e., by using the sensor as a pulser.
2. Sensor: The sensor, also called a transducer, converts the acoustic emission signal to an electrical signal, such as a voltage. AE sensors that are suitable for use as tooth crack detectors are commercially available, e.g., from Physical Acoustics Corp. (PAC) of Princeton, N.J. ("Acoustic Emission Sensors", http://www.pacndt.com/index.aspx?go=products&focus=Sensors.htm). PAC makes miniature sensors as small as the dimensions of a tooth. For example, PAC Model S9225 has a diameter of 3.6 mm (0.15 in.) and a height of 2.4 mm (0.1 in.)("Miniature Sensors", http://www.pacndt.com/index.aspx?go=products&focus=/sensors/miniature.htm).
3. Contact of sensor with teeth: This can be accomplished in several ways, including (a) using a miniature sensor, such as the aforementioned PAC Model S9225, and putting between the sensor and the tooth a coupling agent (e.g., Vaseline® petroleum jelly) which is suitable for use inside a patient's mouth, (b) using a water jet waveguide which, as described in the aforementioned DECI (Dunegan Engineering Company Inc.) report (entitled "AE Waveguides"), operates as follows:

"The water jet enters the fixture from the . . . line where the water surrounds the AE sensor and exits through a nozzle with forced flow toward the test piece. When the (test piece) . . . breaks, AE with high Modal Ratios are detected after propagating through the test piece, up the water column and into the AE sensor."

With respect to such contact of the sensor with teeth, the first and second embodiments utilize method 3(a), and the third embodiment utilizes method 3(b).

4. Electronics and software: The electronics and software perform the following functions: amplification of the electrical signal to a usable level, separation of valid crack growth signals from extraneous noise, signal processing, controls, and displays. The technology for performing these functions has been developed [e.g., Dunegan, U.S. Pat. No. 6,062,083 (May 16, 2000)], and is commercially available (Dunegan Engineering Company Inc., "AE SMART 2000", 2000; "Complete Acoustic Emission Product Line", http://www.pacndt.com/index.aspx?go=products; "Acoustic Emission Testing and Analysis Software", http://www.pacndt.com/index.aspx?go=products&focus=Software.htm). Therefore, the method can be implemented with commercially available hardware and software. The apparatus can be similar to that for prior art AE analyzers, such as that disclosed for bones by Winder, U.S. Pat. No. 6,213,958 B1 (Apr. 10, 2001). It also can use analytical techniques such as neural networks, as disclosed for dental caries detection in U.S. Pat. No. 5,742,700, Yoon et al., Apr. 21, 1998; these techniques have been implemented in commercially available software (e.g., "Acoustic Emission Testing and Analysis Software", http://www.pacndt.com/index.aspx?go=products&focus=Software.htm). The approach herein includes an embodiment in which a baseline reading is on a tooth is obtained, e.g., immediately after a restoration is put on a patient's tooth. This reading is stored and compared with subsequent readings recorded at intervals predetermined by the practicing dentist (for example, at semi-annual cleaning appointments or annual dental examinations); changes may indicate the formation and growth of a crack.

The approach to embodying the stressor, the sensor, and the contact of the sensor with the teeth is to integrate the sensor into existing dental instruments. Exemplary embodiments of the invention are shown in FIGS. 1-5.

FIG. 1 shows an embodiment of the apparatus of the invention in use in a dental instrument similar in appearance, but not in purpose, to that as illustrated in, e.g., above-referenced Angus patent U.S. Pat. No. 4,828,494. Here, a ball 25 is coupled to the end of a handle 23 which encases an electric signal-carrying cable 28. In the present invention, the patient bites on the ball with opposing teeth 10 and 11 between the patient's gums 12. The purpose of having the patient bite on the ball is to stress the tooth so that it produces an acoustic signal (that is, the crack in the tooth grows or otherwise changes, i.e., "talks"), and not to produce pain as performed in Angus patent U.S. Pat. No. 4,828,494, because the present invention is directed to the detection of a crack before it grows large enough as to cause pain. Accordingly and to effect the aims of the present invention, an AE sensor (transducer) 26 is placed in ball 25 in any convenient manner, so that the acoustic signal is transmitted to the AE sensor, such as those described with respect to the Physical Acoustics Corp. (PAC) products referenced above. A coupling agent 30, such as Vaseline® petroleum jelly which is hygienically suitable for use inside a patient's mouth and illustrated in darkened underlining, is placed between the ball and teeth 10, 11 to improve the acoustic coupling and, thereby, to enhance the transfer of the AE signal from the tooth or teeth to the sensor. The sensor converts the acoustic signal emanating from the patient's tooth to an electrical signal, which is conveyed by electrical cable 28 to an AE electronics/software unit 29 such as described above with respect to DECI (Dunegan Engineering Company Inc.) and PAC (Physical Acoustics Corp.) devices. The shape, for example a hemispherically capped cylinder, and flexibility of ball 25 are selected to be appropriate for enclosing and ensuring contact with the AE sensor.

Figure 2:
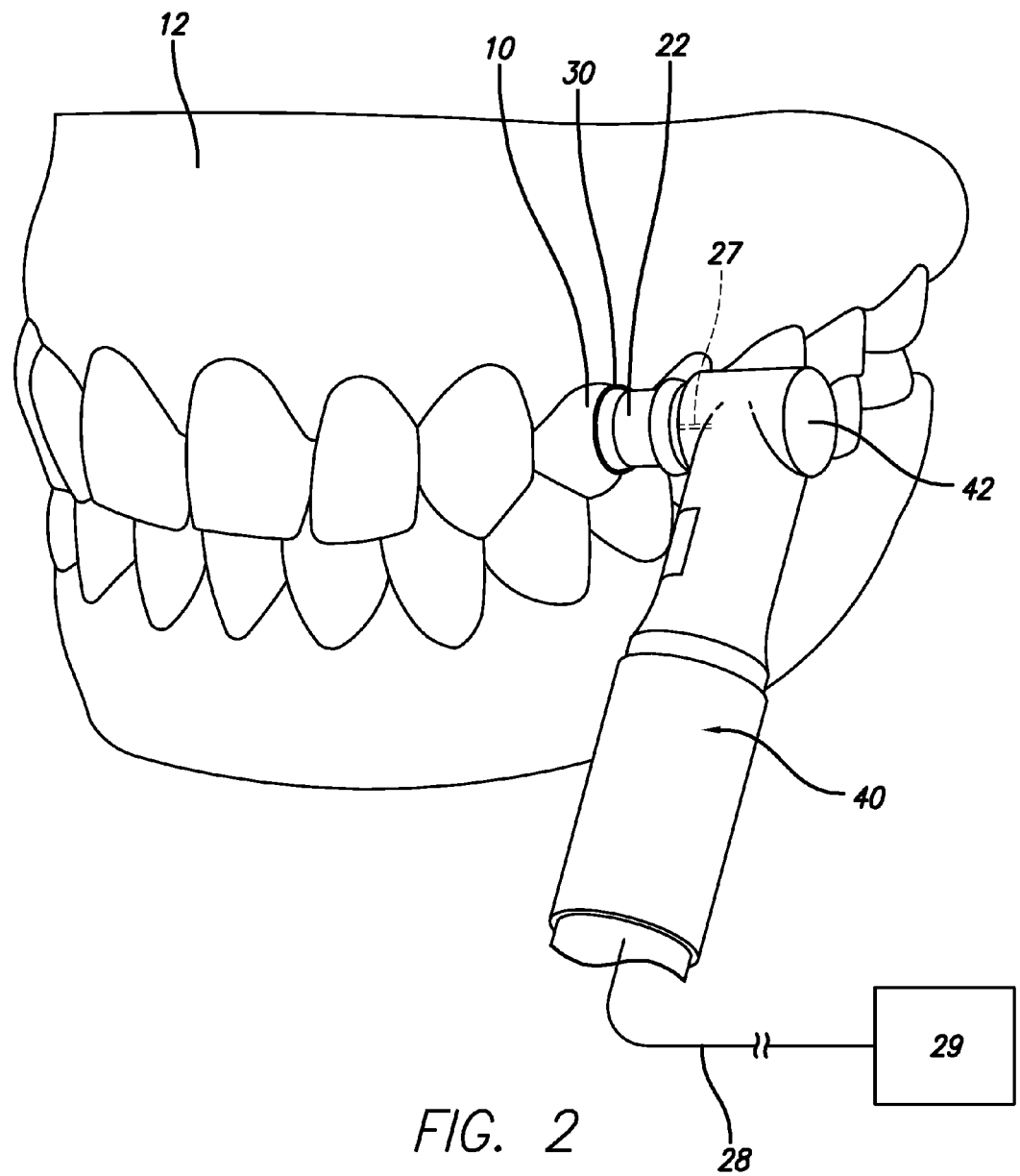
FIG. 2 shows a second embodiment of the apparatus of the invention in use as integrated into a tooth polisher.
Figure 3:
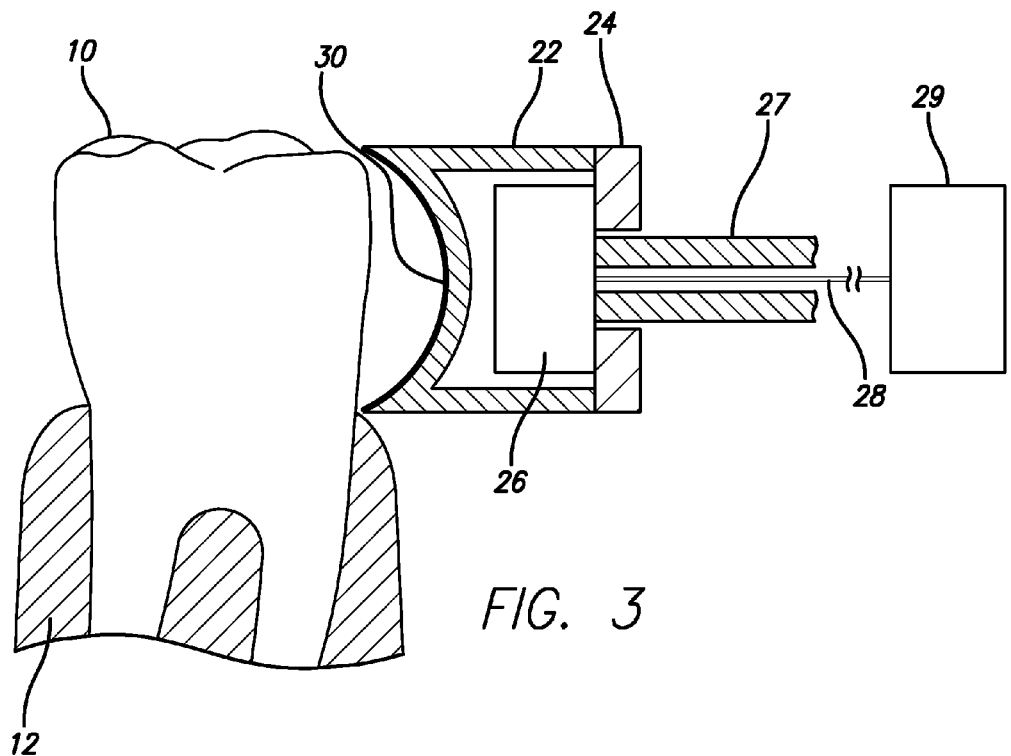
FIGS. 3-4 show the components of the embodiment of the apparatus of the invention as illustrated in FIG. 2.
Figure 4:
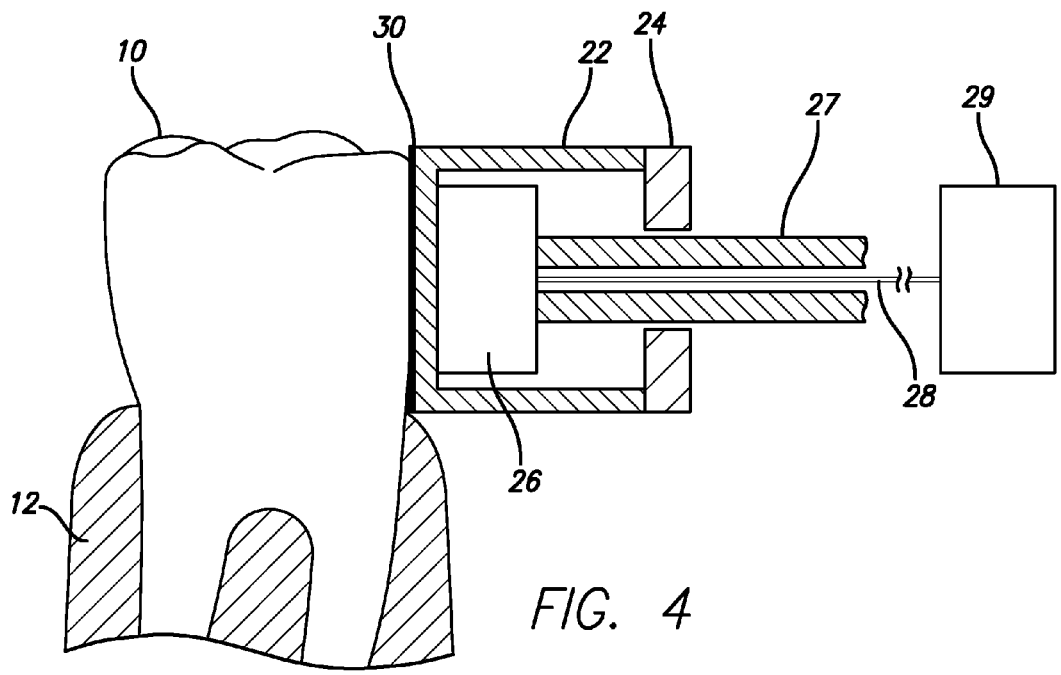

FIGS. 2-4 show the device integrated into a tooth polisher 40 of conventional construction (such as suggested in U.S. Pat. No. 4,014,100) having a head 42 and a flexible cup 22 extending therefrom. As with the embodiment depicted in FIG. 1, a coupling agent 30 may be placed between the flexible cup and tooth 10 to improve the acoustic coupling and, thereby, to enhance the transfer of the AE signal from the tooth to the sensor. FIG. 2 shows the invention in use as placed on a patient's tooth, and FIGS. 3-4 show the components of the invention. In FIGS. 3-4, the tooth and gum 12 are viewed from the side, and flexible cup 22 is in contact with the tooth. The flexible cup is sealed against a base 24. AE sensor 26 is located inside head 42 of tooth polisher 40. A plunger 27 is disposed to press AE sensor 26 against flexible cup 22, in turn to apply force to the flexible cup and to depress it against tooth 10. When plunger 27 is integrated within head 42, such pressing can be manually performed by an operator's hand holding polisher 40 and moving it against the patient's tooth. This action provides a controllable, measurable, and repeatable means of stressing the tooth. FIG. 3 shows the plunger retracted, and FIG. 4 shows the plunger extended, pressing and deforming flexible cup 22 against tooth 10. Plunger 27 is hollow, to provide access to AE sensor 26 and for enabling its electrical cable 28, as electrically and physically coupled to the AE sensor, to electrically mate sensor 26 to electronics/software box 29.

Figure 5:
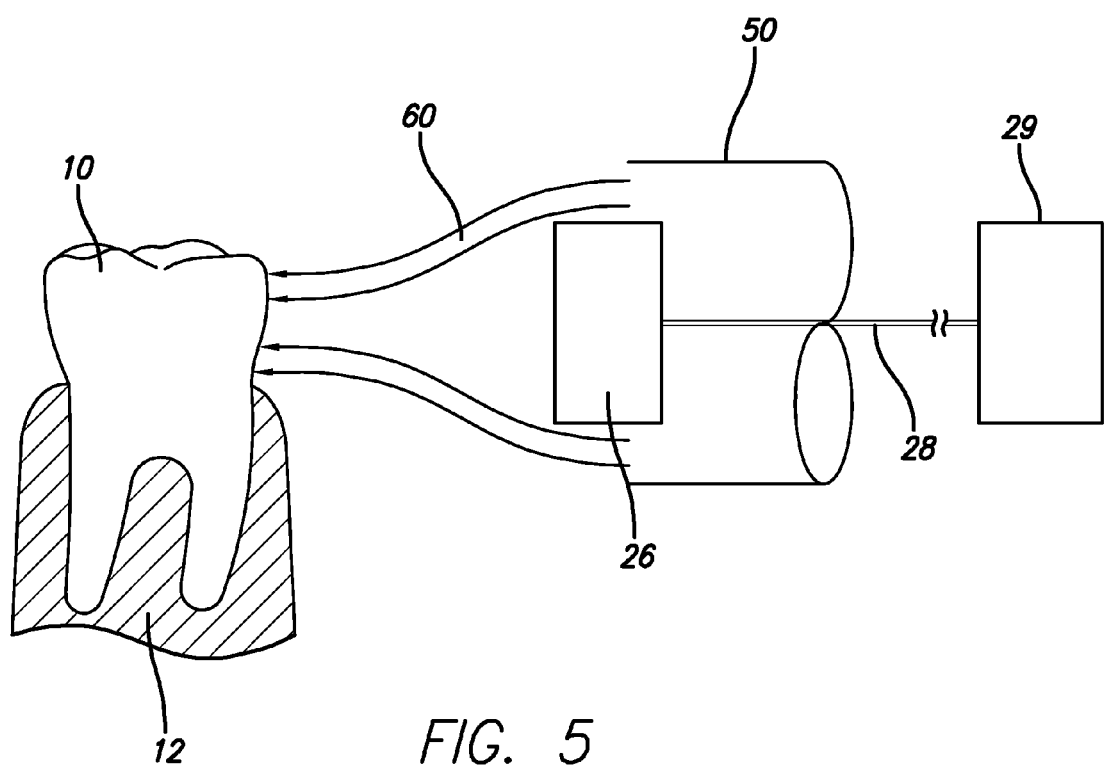
FIG. 5 is a sketch of a third embodiment of the apparatus of the invention, as integrated into a water syringe.

FIG. 5 shows a third embodiment of the inventive device as integrated into a dental water syringe 50 of conventional construction, e.g., U.S. Pat. Nos. 3,393,676 and 3,874,083. A water jet, as depicted by curved arrow-headed lines 60, serves the dual purposes of (1) stressing the tooth in a controllable, measurable, and repeatable way and (2) providing a waveguide to transmit the AE signal from the tooth to AE sensor 26 and, thence, through electrical cable 28 to electronics/software box 29. Thus, the acoustic signal propagates up the water column and into the AE sensor.

Accordingly, although the invention has been described with respect to particular method and apparatus embodiments thereof, it should be realized that various changes and modifications may be made therein without departing from the spirit and scope of the invention.

What is claimed is:

1. A method for detecting a crack in a tooth in a patient, comprising the steps of:
   physically stressing the tooth to cause the crack to grow without causing the tooth to be destroyed and, thereby, to produce an acoustic emission signal from the growth in the crack; and
   analyzing the acoustic emission signal.

2. The method according to claim 1 in which said step of tooth stressing comprises the step of biting an acoustic emission device by the tooth by the patient.

3. The method according to claim 1 in which said tooth stressing step comprises the step of applying pressure through an acoustic emission device onto the tooth.

4. The method according to claim 1 in which said tooth stressing step comprises the steps of utilizing a pulsing sensor, and emitting a pulse from the sensor onto the tooth.

5. The method according to claim 4 in which said sensor utilizing step comprises the steps of contacting the tooth with the sensor and putting, between the sensor and the tooth, a coupling agent which is hygienically suitable for use inside the patient's mouth.

6. The method according to claim 5 in which the coupling agent comprises a petroleum jelly.

7. The method according to claim 4 in which said sensor utilizing step comprises the step of contacting the tooth with a water jet waveguide.

8. The method according to claim 1 further comprising the steps of procedurally obtaining a baseline measurement by the substeps of:
   (i) performing a test on the tooth at a time when the tooth is known not be cracked;
   (ii) recording the baseline measurement as having an acoustic emission signature;
   (iii) repeating said substeps (i) and (ii) at predetermined intervals to obtain subsequent measurements; and
   (iv) comparing the subsequent measurements with the baseline measurement to identify any changes that indicate the initiation and growth of a crack.

9. The method according to claim 8 wherein said procedurally obtained steps are performed at times when the tooth is known not be cracked and when a restoration is placed on the tooth.

10. A method for analyzing a tooth in a patient, comprising the steps of:
  physically stressing the tooth by an acoustic emission process for determining the physical condition thereof without causing it to be destroyed; and
  observing the results thereof.

11. The method according to claim 10 wherein said stressing and observing steps comprise the steps of procedurally obtaining a baseline measurement by the substeps of:
  (i) performing a test on the tooth at a time when the tooth is known not be cracked;
  (ii) recording the baseline measurement as having an acoustic emission signature;
  (iii) repeating said substeps (i) and (ii) at predetermined intervals to obtain subsequent measurements; and
  (iv) comparing the subsequent measurements with the baseline measurement to identify any changes that indicate the initiation and growth of a crack.

12. A method for detecting a crack in a tooth in a patient, in which the tooth is covered by a restoration, comprising the steps of:
  physically stressing the tooth as covered by the restoration to produce an acoustic emission signal therefrom without causing the tooth to be destroyed; and
  analyzing the acoustic emission signal.

13. An apparatus for detecting a crack in a tooth in a patient, comprising:
  a dental stress-applying instrument by which stresses can be applied to the tooth so as to cause the crack to grow without causing the tooth to be destroyed and thereby to produce acoustic emission therefrom; and
  an acoustic emission sensor coupled to said dental instrument for detecting any crack growth resulting from the stresses applied to the tooth.

14. The apparatus according to claim 13 in which said dental instrument comprises a tooth polisher and accompanying cup for applying pressing stresses upon the tooth.

15. The apparatus according to claim 13 in which said dental instrument comprises a water syringe by which the tooth stressing is accomplished by spraying a water jet from said water syringe onto the tooth.

16. An apparatus for detecting a crack in a tooth in a patient including:
  a dental stress-applying instrument comprising a device adapted to apply a stress upon the tooth by a patient biting on said device and thereby to produce a growth in any crack in the tooth without causing the tooth to be destroyed; and
  an acoustic emission sensor coupled to said dental instrument for detecting any such crack growth resulting from the stresses applied to the tooth.

17. An apparatus for detecting a crack in a tooth in a human patient, in which the tooth is covered by a restoration, comprising:
  a dental stress-applying instrument by which stresses can be applied to the tooth as covered by the restoration and thereby to produce a growth in any crack in the tooth without causing the tooth to be destroyed; and
  an acoustic emission sensor coupled to said dental instrument for detecting any such crack growth resulting from the stresses applied to the tooth.

18. The apparatus according to claim 17 further including an acoustic pulser accompanying said acoustic emission sensor.

* * * * *